(12) United States Patent
Miller et al.

(10) Patent No.: US 11,583,412 B2
(45) Date of Patent: Feb. 21, 2023

(54) FUSION CAGE WITH INTEGRATED FIXATION AND INSERTION FEATURES

(71) Applicant: Stryker European Operations Holdings LLC, Kalamazoo, MI (US)

(72) Inventors: M. Todd Miller, Franklin Lakes, NJ (US); Amir Ali Sharifi-Mehr, Bloomingdale, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 0 days.

(21) Appl. No.: 17/155,756

(22) Filed: Jan. 22, 2021

(65) Prior Publication Data

US 2021/0137701 A1 May 13, 2021

Related U.S. Application Data

(63) Continuation of application No. 15/988,276, filed on May 24, 2018, now Pat. No. 10,959,855.
(Continued)

(51) Int. Cl.
*A61F 2/44* (2006.01)
*A61F 2/46* (2006.01)
(Continued)

(52) U.S. Cl.
CPC ............ *A61F 2/4455* (2013.01); *A61B 17/80* (2013.01); *A61F 2/34* (2013.01); *A61F 2/442* (2013.01);
(Continued)

(58) Field of Classification Search
CPC ............... A61F 2/4611; A61F 2/442; A61F 2002/4435; A61F 2002/30561; A61B 17/8875; B33Y 10/00; B33Y 80/00
(Continued)

(56) References Cited

U.S. PATENT DOCUMENTS

| 5,286,573 A | 2/1994 | Prinz et al. |
| 5,411,523 A | 5/1995 | Goble |

(Continued)

FOREIGN PATENT DOCUMENTS

| DE | 102008024281 A1 | 12/2009 |
| DE | 102008024288 A1 | 12/2009 |

(Continued)

OTHER PUBLICATIONS

ACP 1 Anterior Cervical Plating System, Surgical Technique, Stryker Spine, 2016.
(Continued)

*Primary Examiner* — Eduardo C Robert
*Assistant Examiner* — Christina NegrelliRodriguez
(74) *Attorney, Agent, or Firm* — Lerner, David, Littenberg, Krumholz & Mentlik, LLP

(57) ABSTRACT

A surgical implant system includes an implant and a fixation member for securing the implant to tissue. The implant and the fixation member together comprise a single monolithic structure. The implant includes an insertion instrument. The implant, the fixation member, and the insertion instrument together comprise a single monolithic structure and are constructed from a single material. The implant is monolithically connected to the fixation member at a first frangible connection and is monolithically connected to the insertion instrument at a second frangible connection. Each of the frangible connections can be broken when force is applied.

20 Claims, 10 Drawing Sheets

Related U.S. Application Data

(60) Provisional application No. 62/511,101, filed on May 25, 2017.

(51) Int. Cl.
  *A61B 17/80* (2006.01)
  *A61F 2/34* (2006.01)
  *A61F 2/30* (2006.01)
  *A61B 17/88* (2006.01)
  *B33Y 80/00* (2015.01)
  *B33Y 10/00* (2015.01)

(52) U.S. Cl.
  CPC ......... *A61F 2/4611* (2013.01); *A61B 17/8875* (2013.01); *A61F 2/30771* (2013.01); *A61F 2002/3006* (2013.01); *A61F 2002/30561* (2013.01); *A61F 2002/3403* (2013.01); *A61F 2310/00023* (2013.01); *A61F 2310/00179* (2013.01); *A61F 2310/00329* (2013.01); *B33Y 10/00* (2014.12); *B33Y 80/00* (2014.12)

(58) Field of Classification Search
  USPC .......................................... 623/17.11–17.16
  See application file for complete search history.

(56) References Cited

U.S. PATENT DOCUMENTS

| | | |
|---|---|---|
| 5,534,031 A | 7/1996 | Matsuzaki et al. |
| 5,595,703 A | 1/1997 | Swaelens et al. |
| 5,733,286 A | 3/1998 | Errico et al. |
| 5,768,134 A | 6/1998 | Swaelens et al. |
| 5,943,235 A | 8/1999 | Earl et al. |
| 5,968,098 A | 10/1999 | Winslow |
| 6,010,502 A | 1/2000 | Bagby |
| 6,039,762 A | 3/2000 | McKay |
| 6,231,611 B1 | 5/2001 | Mosseri |
| 6,391,058 B1 | 5/2002 | Kuslich et al. |
| 6,432,107 B1 | 8/2002 | Ferree |
| 6,520,996 B1 | 2/2003 | Manasas et al. |
| 6,530,955 B2 | 3/2003 | Boyle et al. |
| 6,530,956 B1 | 3/2003 | Mansmann |
| 6,645,227 B2 | 11/2003 | Fallin et al. |
| 6,716,247 B2 | 4/2004 | Michelson |
| 6,758,849 B1 | 7/2004 | Michelson |
| 7,070,601 B2 | 7/2006 | Culbert et al. |
| 7,081,120 B2 | 7/2006 | Li et al. |
| 7,238,206 B2 | 7/2007 | Lange et al. |
| 7,509,183 B2 | 3/2009 | Lin et al. |
| 7,537,664 B2 | 5/2009 | O'Neill et al. |
| 7,665,979 B2 | 2/2010 | Heugel |
| 7,850,733 B2 | 12/2010 | Baynham et al. |
| 7,909,872 B2 | 3/2011 | Zipnick et al. |
| 8,062,375 B2 | 11/2011 | Glerum et al. |
| 8,275,594 B2 | 9/2012 | Lin et al. |
| 8,349,015 B2 | 1/2013 | Bae et al. |
| 8,382,842 B2 | 2/2013 | Greenhalgh et al. |
| 8,398,713 B2 | 3/2013 | Weiman |
| 8,403,986 B2 | 3/2013 | Michelson |
| 8,435,298 B2 | 5/2013 | Weiman |
| 8,439,977 B2 | 5/2013 | Kostuik et al. |
| 8,449,585 B2 | 5/2013 | Wallenstein et al. |
| 8,584,853 B2 | 11/2013 | Knight et al. |
| 8,585,761 B2 | 11/2013 | Theofilos |
| 8,590,157 B2 | 11/2013 | Kruth et al. |
| 8,673,011 B2 | 3/2014 | Theofilos et al. |
| 8,697,231 B2 | 4/2014 | Longepied et al. |
| 8,734,491 B2 | 5/2014 | Seavey |
| 8,784,721 B2 | 7/2014 | Philippi et al. |
| 8,801,791 B2 | 8/2014 | Soo et al. |
| 8,814,919 B2 | 8/2014 | Barrus et al. |
| 8,843,229 B2 | 9/2014 | Vanasse et al. |
| 8,870,957 B2 | 10/2014 | Vraney et al. |
| 8,903,533 B2 | 12/2014 | Eggers et al. |
| 8,932,356 B2 | 1/2015 | Kraus |
| 8,967,990 B2 | 3/2015 | Weidinger et al. |
| 8,999,711 B2 | 4/2015 | Harlow et al. |
| 9,011,982 B2 | 4/2015 | Muller et al. |
| 9,135,374 B2 | 9/2015 | Jones et al. |
| 9,180,010 B2 | 11/2015 | Dong et al. |
| 9,283,078 B2 | 3/2016 | Roels et al. |
| 9,456,901 B2 | 10/2016 | Jones et al. |
| 9,480,577 B2 | 11/2016 | Despiau et al. |
| 2001/0047207 A1 | 11/2001 | Michelson |
| 2001/0047208 A1 | 11/2001 | Michelson |
| 2002/0128714 A1 | 9/2002 | Manasas et al. |
| 2003/0040798 A1 | 2/2003 | Michelson |
| 2003/0135276 A1 | 7/2003 | Eckman |
| 2004/0024400 A1 | 2/2004 | Michelson |
| 2004/0243237 A1 | 12/2004 | Unwin et al. |
| 2004/0249471 A1 | 12/2004 | Bindseil et al. |
| 2005/0021151 A1 | 1/2005 | Landis |
| 2005/0149192 A1 | 7/2005 | Zucherman et al. |
| 2005/0177238 A1 | 8/2005 | Khandkar et al. |
| 2007/0233272 A1 | 10/2007 | Boyce et al. |
| 2009/0093881 A1 | 4/2009 | Bandyopadhyay et al. |
| 2009/0222100 A1 | 9/2009 | Cipoletti et al. |
| 2009/0291308 A1 | 11/2009 | Pfister et al. |
| 2010/0100131 A1 | 4/2010 | Wallenstein |
| 2010/0137990 A1 | 6/2010 | Apatsidis et al. |
| 2010/0228369 A1 | 9/2010 | Eggers et al. |
| 2010/0312282 A1 | 12/2010 | Abdou |
| 2011/0144752 A1 | 6/2011 | Defelice et al. |
| 2011/0165340 A1 | 7/2011 | Baumann |
| 2011/0168091 A1 | 7/2011 | Baumann et al. |
| 2011/0172774 A1 | 7/2011 | Varela |
| 2011/0190904 A1 | 8/2011 | Lechmann et al. |
| 2011/0301709 A1 | 12/2011 | Kraus et al. |
| 2012/0046750 A1 | 2/2012 | Obrigkeit et al. |
| 2012/0143334 A1 | 6/2012 | Boyce et al. |
| 2012/0158062 A1 | 6/2012 | Nunley et al. |
| 2012/0179261 A1 | 7/2012 | Soo |
| 2012/0191188 A1 | 7/2012 | Huang |
| 2012/0191189 A1 | 7/2012 | Huang |
| 2012/0310364 A1 | 12/2012 | Li et al. |
| 2013/0046345 A1 | 2/2013 | Jones et al. |
| 2013/0110243 A1 | 5/2013 | Patterson et al. |
| 2013/0116793 A1 | 5/2013 | Kloss |
| 2013/0171019 A1 | 7/2013 | Gessler et al. |
| 2013/0197645 A1 | 8/2013 | Assell et al. |
| 2013/0245697 A1 | 9/2013 | Hulliger |
| 2013/0273131 A1 | 10/2013 | Frangov et al. |
| 2014/0086780 A1 | 3/2014 | Miller et al. |
| 2014/0088716 A1 | 3/2014 | Zubok et al. |
| 2014/0107785 A1 | 4/2014 | Geisler et al. |
| 2014/0107786 A1 | 4/2014 | Geisler et al. |
| 2014/0172111 A1 | 6/2014 | Lang et al. |
| 2015/0018956 A1 | 1/2015 | Steinmann et al. |
| 2015/0045924 A1 | 2/2015 | Cluckers et al. |
| 2015/0134063 A1 | 5/2015 | Steinmann et al. |
| 2015/0142158 A1 | 5/2015 | Szwedka |
| 2015/0352784 A1 | 12/2015 | Lechmann et al. |
| 2015/0367575 A1 | 12/2015 | Roels et al. |
| 2016/0058575 A1 | 3/2016 | Sutterlin, III et al. |
| 2016/0157908 A1 | 6/2016 | Cawley et al. |
| 2017/0071753 A1 | 3/2017 | Josse et al. |
| 2017/0325966 A1* | 11/2017 | Capote ................ A61B 17/808 |
| 2019/0038318 A1 | 2/2019 | Tempco et al. |
| 2019/0105172 A1* | 4/2019 | Sournac ................ A61F 2/447 |

FOREIGN PATENT DOCUMENTS

| | | |
|---|---|---|
| EP | 0425542 B1 | 3/1995 |
| EP | 1464307 A1 | 10/2004 |
| EP | 1905391 B1 | 1/2010 |
| EP | 2145913 A1 | 1/2010 |
| EP | 2457538 A1 | 5/2012 |
| EP | 1772108 B1 | 11/2015 |
| JP | 2007-275571 A | 10/2007 |
| JP | 2013-528111 A | 7/2013 |
| JP | 2013-532024 A | 8/2013 |
| JP | 2015-208566 A | 11/2015 |
| WO | 9000037 A1 | 1/1990 |

(56) References Cited

FOREIGN PATENT DOCUMENTS

| WO | 9405235 A1 | 3/1994 |
|---|---|---|
| WO | 9419174 A1 | 9/1994 |
| WO | 9510248 A1 | 4/1995 |
| WO | 9532673 A1 | 12/1995 |
| WO | 9608360 A1 | 3/1996 |
| WO | 9628117 A1 | 9/1996 |
| WO | 9640015 A1 | 12/1996 |
| WO | 9640019 A1 | 12/1996 |
| WO | 9734546 A1 | 9/1997 |
| WO | 0025707 A1 | 5/2000 |
| WO | 0040177 A1 | 7/2000 |
| WO | 0066045 A1 | 11/2000 |
| WO | 0202151 A2 | 1/2002 |
| WO | 0230337 A2 | 4/2002 |
| WO | 02080820 A1 | 10/2002 |
| WO | 2006101837 A2 | 9/2006 |
| WO | 2009068021 A1 | 6/2009 |
| WO | 2011030017 A1 | 3/2011 |
| WO | 2011156504 A2 | 12/2011 |
| WO | 201317647 A1 | 2/2013 |
| WO | 2013155500 A1 | 10/2013 |
| WO | 2013156545 A1 | 10/2013 |
| WO | 201496294 A1 | 6/2014 |
| WO | 2014145527 A2 | 9/2014 |

OTHER PUBLICATIONS

Akamaru et al., Healing of Autologous Bone in a Titanium Mesh Cage Used in Anterior Column Reconstruction After Total Spondylectomy; SPINE vol. 27, No. 13, pp. E329-E333, 2002.

Bridwell et al.., Specialty Update, What's New in Spine Surgery, The Journal of Bone and Joint Surgery, Incorporated, pp. 1022-1030, Core 1st page of article, Jun. 2015.

Cheung et al., Spinal Instrumentation Overview in Lumbar Degenerative Disorders: Cages, Lumbar Spine: Official Publication of the International Society for the Study of Lumbar Spine (3), pp. 286-291, 2004.

Chong et al., The design evolution of interbody cages in anterior cervical discectomy and fusion: a systematic review; BMC Musculoskeletal Disorders Apr. 2015 16:99, pp. 1-20.

Costa et al., Stand-alone cage for posterior lumbar interbody fusion in the treatment of high-degree degenerative disc disease: design of a new device for an "old" technique. A prospective study on a series of 116 patients, Eur Spine J, May 2011: 20 (Suppl 1), pp. 46-56.

Cunningham et al., Design of Interbody Fusion Cages: Historical Considerations and Current Perspectives in Cage Technology; Surgical Techniques, Spinal Implants, pp. 421-465, 2006.

EBI Spine, Promotional flyer, 1 page 2005.

Extended European Search Report and Written Opinion for EP Application No. 18173999.6, dated Nov. 19, 2018.

Extended European Search Report for EP 16 15 2952 dated Jul. 1, 2016.

Fukuda A, Takemoto M, Tanaka K, Fujibayashi S, Pattanayak DK, Matsushita T, Sasaki K, Nishida N, Kokubo T, Nakamura T. Bone ingrowth into pores of lotus stem-type bioactive titanium implants fabricated using rapid prototyping technique. Bioceramics Development and Applications. Jan. 1, 2011;1, 3 pages.

Kim et al. Spinal Instrumentation Surgical Techniques, Thieme Medical publishers, 2004, pp. 232-245, 518-524, p. 32-537, 736-743, 795-800.

Kuslich, Lumbar Interbody Cage Fusion for Back Pain: An Update on the Bak (Bagby and Kuslich) System, SPINE: State of the Art Reviews; vol. 13, No. 2, May 1999, pp. 295-311.

Lin et al., Interbody Fusion Cage Design Using Integrated Global Layout and Local Microstructure Topology Optimization; SPINE, vol. 29, No. 16, pp. 1747-1754, 2004.

Lin, et al. Structural and mechanical evaluations of a topology optimized titanium interbody fusion cage fabricated by selective laser melting process, Journal of Biomedical Materials Research Part A DOI 10.1 002/jbm.a, pp. 272-279, Apr. 2007.

McAfee, Interbody Fusion Cages in Reconstructive Operations on the Spine, The Journal of Bone and Joint Surgery Incorporated, vol. 81A, No. 6, Jun. 1999, pp. 859-880.

Sasso, Screws, Cages or Both?, <http://www.spineuniverse.com/professional/technology/surgical/thoracic/>, pp. 1-11, Sep. 2012.

Schultz, Christian K., et al., U.S. Appl. No. 62/478,162, filed Mar. 29, 2017, titled "Spinal Implant System".

Sofamar Danek Interfix Thread Fusion Device, pp. 32-45, 1999.

Stryker, Tlritanium basic science summary, technical monograph, pp. 1-2, 2016.

Synthes Contact Fusion Cage, Technique Guide, 2007, pp. 1-16.

Williams et al., CT Evaluation of Lumbar Interbody Fusion: Current Concepts, AJNR Am J Neuroradiol 26:2057-2066, Sep. 2005.

Willis, Steven, et al., U.S. Appl. No. 14/994,749, filed Jan. 13, 2016, titled "Spinal Implant With Porous and Solid Surfaces".

Zdeblick, et al., LT-CAGE Lumbar Tapered Fusion Device Surgical Technique, Medtronic, pp. 1-25, 2000.

\* cited by examiner

FUSION CAGE WITH INTEGRATED FIXATION AND INSERTION FEATURES

CROSS REFERENCE TO RELATED APPLICATION

The present application is a continuation of U.S. patent application Ser. No. 15/988,276, filed May 24, 2018, which claims the benefit of the filing date of U.S. Provisional Patent Application No. 62/511,101 filed May 25, 2017, the disclosure of which is hereby incorporated herein by reference.

BACKGROUND OF THE INVENTION

The present inventions relate, in general, to surgical implant systems and methods of implanting same. More particularly, the present inventions relate to surgical implant systems including monolithic structures having an implant, a fixation member, and/or an instrument that are frangibly connected for separation during a surgical procedure.

Surgical implants often include several components. The implant itself may be comprised of different pieces, and is often secured to adjacent tissue by one or more additional fixation elements, such as screws or anchors. In addition, one or more instruments are typically needed during a surgical procedure to grasp and guide the implant and to place the fixation element(s) to secure the implant. The many components needed during one procedure can pose challenges for organization in the operating room, sterilization to prevent infection, and accuracy and efficiency in properly handling and placing the implant and fixation element(s) during a procedure. For instance, dropping or mishandling smaller screws can be a challenge during a procedure. This increases manufacturing costs as well as inventory of implants and instrumentation.

There is a need in the art for a surgical implant system that overcomes these drawbacks by simplifying surgical procedures and by making such procedures more efficient.

SUMMARY OF THE INVENTION

A first aspect of the present disclosure is a surgical implant system that includes an implant, a fixation member for securing the implant to tissue, and an insertion instrument. The implant, the fixation member, and the insertion instrument together comprise a single monolithic structure.

In other embodiments, the implant may be monolithically connected to the fixation member at a first frangible connection. The first frangible connection may be sheared through application of torque applied to the fixation member. The implant may be monolithically connected to the insertion instrument at a second frangible connection. The second frangible connection may be broken through application of a force applied to the insertion instrument. The implant may be one of a spinal implant, a cortical plate, and an acetabular cup.

The surgical implant system may be manufactured by three-dimensional (3D) printing. The surgical implant system may be manufactured by additive layer manufacturing. The system may be constructed of a single material.

A second aspect of the present disclosure is a surgical implant system that includes an implant and an insertion instrument. The implant and the insertion instrument together comprise a single monolithic structure.

In other embodiments, the system may be constructed of a single material.

A third aspect of the present disclosure is a surgical implant system that includes an implant and a fixation member for securing the implant to tissue. The implant and the fixation member together comprise a single monolithic structure.

In other embodiments, the surgical system may include an insertion instrument. The implant, the fixation member, and the insertion instrument together may comprise a single monolithic structure. The system may be constructed of a single material. The implant may be monolithically connected to the fixation member at a first frangible connection. The first frangible connection may be sheared through application of torque applied to the fixation member. The implant may be monolithically connected to the insertion instrument at a second frangible connection. The second frangible connection may be broken through application of a force applied to the insertion instrument. The implant may be one of a spinal implant, a cortical plate, and an acetabular cup. The implant system may be manufactured by 3-D printing. The surgical system may be manufactured by additive layer manufacturing.

Another aspect of the present disclosure is a method of manufacturing a surgical implant system including constructing the surgical implant system by additive layer manufacturing to include an implant and a fixation member for securing the implant to tissue. The implant is monolithically connected to the fixation member at a first frangible connection, such that the implant and the fixation member together comprise a single monolithic structure.

In other embodiments, the method may include the step of constructing the surgical implant to include an insertion instrument. The insertion instrument may be monolithically connected to the implant at a second frangible connection, such that the implant, the fixation member, and the insertion instrument together comprise a single monolithic structure.

Another aspect of the present disclosure is a method of manufacturing a surgical implant system that includes 3-D printing the surgical implant system to include an implant, a fixation member for securing the implant to tissue, and an insertion instrument. The implant is monolithically connected to the fixation member at a first frangible connection and the implant is monolithically connected to the insertion instrument at a second frangible connection, such that the implant, the fixation member, and the insertion instrument together comprise a single monolithic structure.

In other embodiments of the method, the step of 3-D printing may include 3-D printing the surgical implant system of a single material.

Yet another aspect of the present disclosure is a method of manufacturing a surgical implant system that includes constructing the surgical implant system by additive layer manufacturing to include an implant, a fixation member for securing the implant to tissue, and an insertion instrument. The implant is monolithically connected to the fixation member at a first frangible connection and the implant is monolithically connected to the insertion instrument at a second frangible connection, such that that the implant, the fixation member, and the insertion instrument together comprise a single monolithic structure.

In other embodiments of the method, the step of constructing may include constructing the surgical implant system of a single material.

Yet another aspect of the present disclosure is a method of inserting a surgical implant system including implanting a single monolithic structure including an implant, a fixation member for securing the implant to tissue, and an insertion instrument. The implant is monolithically connected to the fixation member at a first frangible connection and the implant is monolithically connected to the insertion instrument at a second frangible connection. The method further includes applying a force to the fixation member to break the first frangible connection and applying a force to the insertion instrument to break the second frangible connection.

Another aspect of the present disclosure is a device for intervertebral disc repair that includes a spacer and a fixation member. The fixation member has an initial condition in which the spacer and the fixation member are monolithically connected and an operative condition in which the fixation member and spacer are separate and distinct.

In other embodiments, the fixation member may have a screw having a central axis. The spacer may define an aperture for receiving the screw, the aperture having a perimeter at a location about a central axis of the aperture that is fully enclosed within the spacer. The central axis of the screw and the central axis of the aperture may extend through an anterior surface of the spacer at a non-perpendicular angle. The spacer may further define a second aperture for receiving a second screw, the second aperture defining a perimeter at a location about a central axis of the second aperture that is fully enclosed within the spacer. The second aperture may have a central axis. The central axis of the screw and the central axis of the second aperture may extend through an anterior surface of the spacer at a second non-perpendicular angle, the first and second non-perpendicular angles being different. The spacer may include a channel for receiving an anchor, the channel being a dovetail slot extending along a superior or an inferior surface of the spacer. The channel may extend between and intersect both an anterior surface and a posterior surface of the spacer. A perimeter of the channel about a central axis of the channel may not be fully enclosed within the spacer at a location about the central axis of the channel. The fixation member may be an anchor blade. The blade may be positioned relatively further from the posterior surface of the spacer when the blade is in the initial condition, and the blade may be positioned relatively closer to the posterior surface when the blade is in the operative condition.

Yet another aspect of the present disclosure is an intervertebral system including a spacer having a recess for receiving a bone anchor and a bone anchor frangibly coupled to the spacer and being movable relative to the spacer. The bone anchor has an initial position in which the bone anchor is positioned with a distal end of the anchor in the recess of the spacer and an operative position in which the anchor is positioned with at least a proximal end of the anchor in the recess. In the initial position the bone anchor and the spacer are monolithically connected.

In other embodiments, movement of the bone anchor from the initial position to the operative position may engage the bone with the bone anchor to secure the spacer to an adjacent vertebra. The movement may include torque of the bone anchor.

Another aspect of the present disclosure is a device for intervertebral repair including a spacer having a posterior surface and an anterior surface and a bone anchor frangibly coupled to the spacer. The bone anchor has an initial position in which the bone anchor is relatively far from the posterior surface of the spacer and an operative position in which the bone anchor is relatively near to the posterior surface of the spacer. In the initial position the bone anchor is monolithically connection with the spacer. The device also includes an insertion instrument that has an initial condition in which the instrument is monolithically connected with the spacer and an operative condition in which the instrument is separate and distinct from the spacer.

In other embodiments, in the initial condition the insertion instrument may be adapted to stabilize the device and/or drive the device into a disc space.

Yet another aspect of the present disclosure is a bone plating system including a plate having a recess for receiving a bone anchor and a fixation member movable relative to the plate. The fixation member has an initial position in which the fixation member is positioned with a distal end thereof in the recess of the plate and an operative position in which the fixation member is positioned with at least a proximal end thereof in the recess. The system includes an insertion instrument that has an initial condition in which the instrument is monolithically connected with the plate and an operative condition in which the instrument is separate and distinct from the plate. In the initial position, the fixation member and plate are monolithically connected.

Another aspect of the present disclosure is a device for intervertebral repair including a spacer having an anterior surface and an insertion instrument. The insertion instrument is frangibly coupled to the anterior surface of the spacer and has an initial condition in which the instrument is monolithically connected with the spacer and an operative condition in which the instrument is separate and distinct from the spacer.

Another aspect of the present disclosure is a method of using an intervertebral device including inserting the device into disc space, the device including a spacer, a bone anchor monolithically coupled to the spacer, and an insertion instrument monolithically coupled to the space; moving the bone anchor relative to the spacer, such that the bone anchor and the spacer become separate and distinct pieces; and bending the insertion instrument such that it breaks apart from the spacer.

In other embodiments, the step of moving the bone anchor may engage the bone anchor to an adjacent vertebra. The step of moving the bone anchor may include rotating the anchor. The step of moving the anchor may include driving the anchor distally. The method may include the step of removing the insertion instrument from a patient.

BRIEF DESCRIPTION OF THE DRAWINGS

A more complete appreciation of the subject matter of the present invention(s) and of the various advantages thereof can be realized by reference to the following detailed description in which reference is made to the accompanying drawings in which.

DETAILED DESCRIPTION

Figure 1:
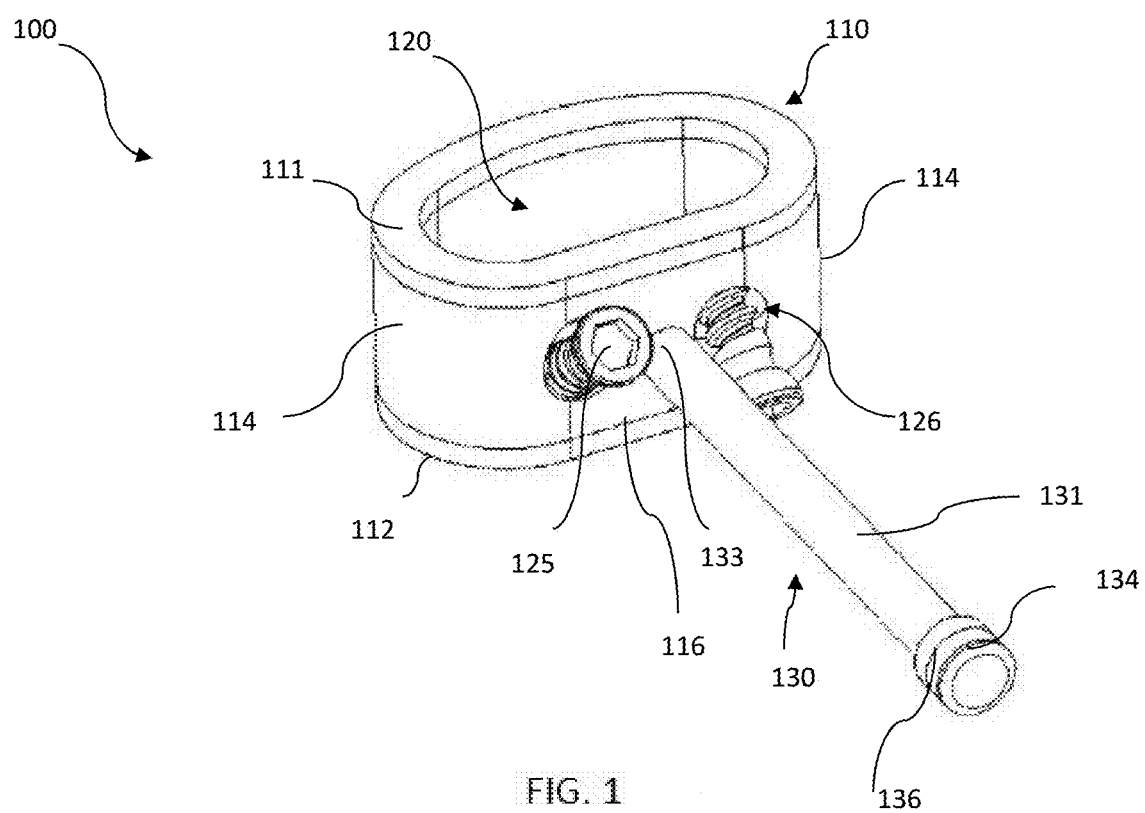
FIGS. 1-5 are front perspective, top perspective, front perspective, enlarged front perspective, and sectional front perspective views, respectively, of an intervertebral implant system according to an embodiment of the present invention.

In describing certain aspects of the present invention(s), specific terminology will be used for the sake of clarity. However, the invention(s) is not intended to be limited to any specific terms used herein, and it is to be understood that each specific term includes all technical equivalents, which operate in a similar manner to accomplish a similar purpose. In the drawings and in the description which follows, the term "proximal" refers to the end of the fixation members and instrumentation, or portion thereof, which is closest to the operator in use, while the term "distal" refers to the end of the fixation members and instrumentation, or portion thereof, which is farthest from the operator in use.

Referring to FIGS. 1-5, an intervertebral implant system 100 according to an embodiment of the present invention includes a monolithic device cast as a single piece including a spacer 110 frangibly connected with fixation members or screws 125 and an insertion instrument 130. System 100, including all components thereof, is made of a single material. A system in accordance with the present inventions can include a single fixation member or two or more fixation members depending on a particular procedure and/or the configuration of the associated implant. Although initially constructed as a single, continuous structure, implant system 100 includes frangible connections between spacer 110 and fixation members 125 and between spacer 110 and instrument 130. The monolithic connection among the different components can be disconnected or broken after spacer 110 is positioned in an intervertebral disc space of the spine. While it will be discussed below that system 100 is produced through additive layer manufacturing (ALM), i.e. 3D printing, it is understood that the single, continuous or monolithic construct is created upon completion of the ALM process. The monolithic construction of system 100 is completed during a single process, which differentiates it from processes of separately manufacturing and later welding together the different components of system 100. Alternate systems in accordance with the present inventions can include a monolithic device cast as a single piece including a spacer 110 frangibly connected with fixation members or screws 125 and omitting an instrument. Systems can also include a monolithic device cast as a single piece including a spacer 110 frangibly connected with an insertion instrument 130 and omitting fixation members.

As described more thoroughly below, implant system 100 is manufactured as a one-piece, integral construct with integrated fixation anchors/screws as well as integrated instrumentation to facilitate implantation. The preferred method of manufacturing system 100 is by utilizing 3D printing technology, which allows system 100 to be made monolithically with all features and components built into system 100 from the start. This improves handling of system 100 during implantation and can streamline the surgical procedure to make it more efficient. Notably, the initial construction and positioning of the fixation anchors/screws in system 100 eliminates the need for guides, such as screw guides, since the fixation elements are already in place for insertion once the main implant is finally seated. System 100 is fully ready to implant immediately out of its packaging, which minimizes steps for the surgeon and is designed to reduce complexity and increase operational efficiency. These benefits extend to all of the present embodiments, as well as to other types of surgical implant systems as contemplated by the present disclosure.

Spacer 110 includes a top or superior bone-contacting surface 111 and a bottom or inferior surface 112, a posterior or leading surface 115, an anterior or trailing surface 116 opposite leading surface 115, and lateral surfaces 114 extending between the leading and trailing surfaces 115, 116. In the illustrated embodiment, spacer 110 has a generally rounded, oblong shape with lateral surfaces 114 being rounded. Alternatively, spacer 110 may be generally, square, rectangular, kidney, oval, circular, or other geometric shape in the superior view. Top and bottom surfaces or endplates 111, 112 may be flat, concave, convex, or any other shape in the anterior or lateral views and may include teeth or ridges for more secure placement against endplates of the adjacent vertebrae. Endplates 111, 112 can be porous to optimize bone growth/fusion. In particular, in a lateral view, top and bottom sides 111, 112 may be curved or angled to give spacer 110 a lordotic shape. Hyperlordotic and double taper implants are also contemplated.

Spacer 110 further defines opening 120 extending from top surface 111 to bottom surface 112. Opening 120 has a generally rounded, oblong shape and is surrounded by inner surface 122. However, in other examples, opening 120 may have any shape or may comprise multiple openings. Opening 120 may allow for receipt of bone in-growth material, such as bone chips, autograft, allograft, Demineralized Bone Matrix (DBM), or synthetics.

Figure 3:
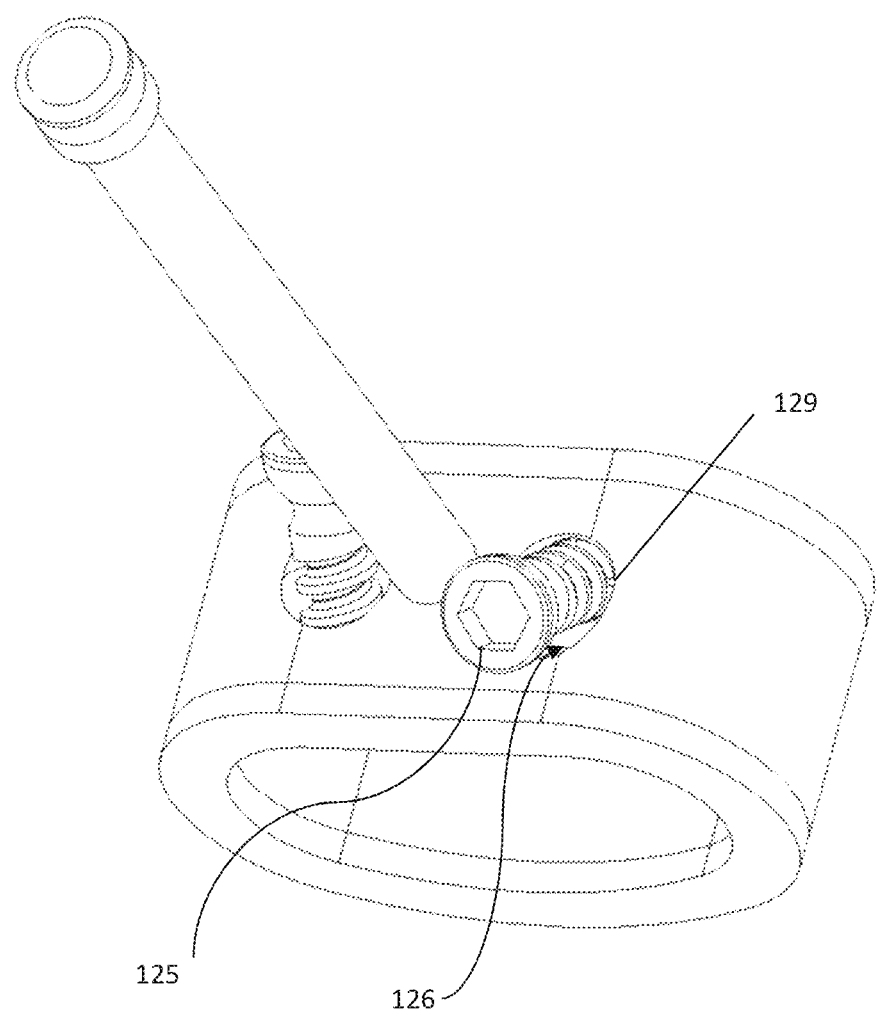

Spacer 110 further includes two screws 125 positioned in respective holes 126, the screws and holes each extending from trailing surface 116 to inner surface 122 and being spaced apart. Holes 126 and screws 125 each extend about a central axis that forms a non-perpendicular angle with trailing surface 116. The angle of the screws and holes can vary as desired, and may be prepared such that the screws can reach the adjacent vertebral endplate to fix spacer 110 to the adjacent vertebra. Each hole 126 may be angled in a different direction from the other hole, and each screw 125 may be angled in a different direction from the other screw. However, in other examples, holes 126 may also extend about a central axis that is substantially perpendicular to trailing surface 116. As shown in FIG. 3, it is preferable that screws 125 are angled in opposite directions to engage both superior and inferior positioned vertebrae. Although the illustrated embodiment has two holes 126 and screws 125, in other arrangements there may be more or less of the holes and screws.

Figure 2:
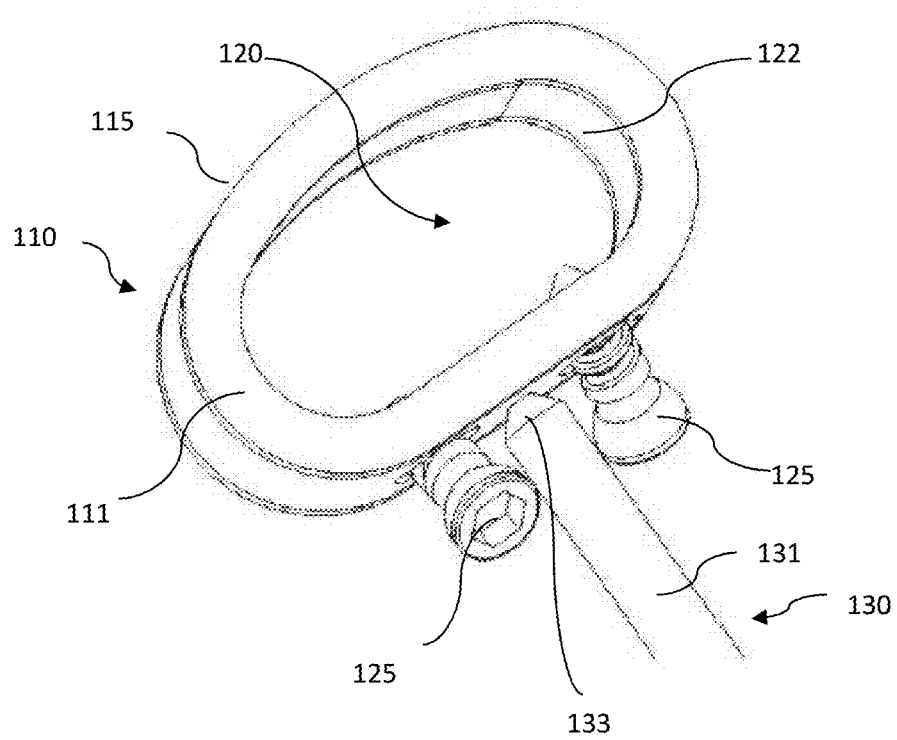
Figure 4:
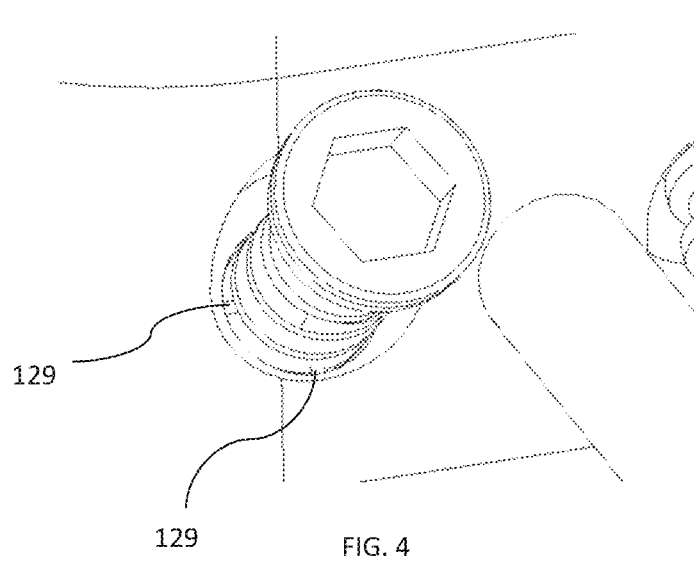
Figure 5:
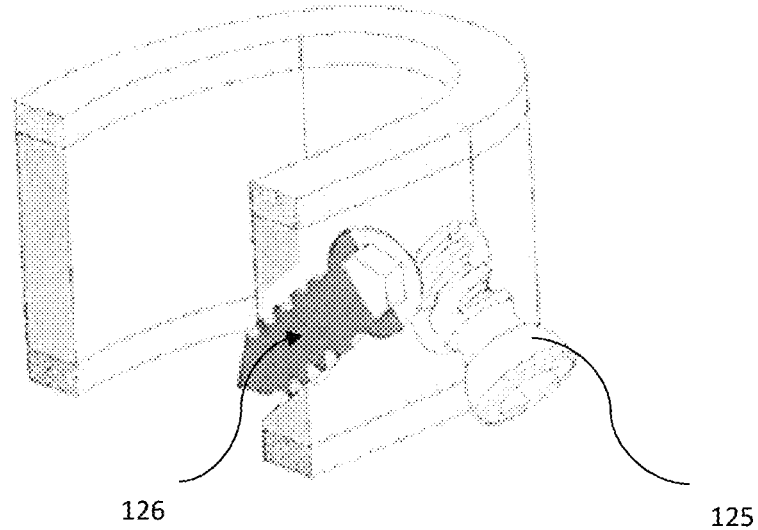

As best shown in FIG. 2, screws 125 are initially monolithically connected with spacer 110 and positioned such that the distal portion of the screw extends through inner surface 122, a portion of the screw shaft being enclosed within hole 126 of spacer 110, and the head and a portion of the shaft is positioned anteriorly external to trailing surface 116. During a 3D printing procedure, spacer 110 and screws 125 are manufactured simultaneously with at least one frangible connection 129 therebetween. This connection can be a relatively thin layer of the material of spacer 110 and screws 125 that bridges or connects adjacent locations between spacer 110 and screws 125. For example, as best shown in FIGS. 3-4, the frangible connection 129 is a radial flange of the material extending from the shaft or a thread on the shaft of screw 125 to a surface of hole 126. This flange can be perpendicular to the screw axis or angled thereto. Of course, multiple connections 129 can be utilized and spaced apart about the circumference of screw 125. A single connection 129 can also be employed. In other embodiments, an annular flange between spacer 110 and screws 125 can be provided via the material during 3D printing. In each case regardless of the geometry and location of the frangible connection, the material at the connection can be selectively constructed to break or shear upon a force applied to one of spacer 110 and screws 125. That is, screws 125 can be torqued to advance them further into holes 126. As screw 125 is torqued, the frangible connection between screw 125 and spacer 110 breaks such that screw 125 becomes a separate piece from spacer 110 and screw 125 is thereafter inserted further into hole 126 and ultimately into communication with an adjacent vertebra.

In the illustrated embodiment, there are two threaded screws 125, angled in opposite directions; however, in other examples there may be more or less of screws 125 and the screws may be angled in different configurations. Screws 125 may include variable and/or fixed angle screws. Further, screws 125 may include self-drilling and/or self-tapping features to facilitate and minimize screw-hole preparation.

Spacer 110 further includes insertion instrumentation 130. Instrument 130 includes shaft 131 extending from a distal end 133 to a proximal end 134. Distal end 133 of shaft 131 is monolithically connected with and coupled to trailing surface 116 in a manner similar to the connection between spacer 110 and screws 125. The monolithic construction of instrument 130 with spacer 110 is strong in both compression and tension forces. That is, the interface between instrument 130 and spacer 110 is such that it can withstand forces applied by a user during a surgical procedure without breaking. As instrument 130 is bent with respect to spacer 110, it breaks off from spacer 110 and can be removed from the patient. Distal end 133 may be tapered, as in FIG. 2, or it may be straight. The taper can be configured to facilitate the ultimate breakage between instrument 130 and spacer 110. In some cases, the taper or the connection in general can be manufactured to be stronger in some planes as opposed to others. That is, it may be easier to bend instrument 130 with respect to spacer 110 at particular angles.

Shaft 131 extends generally orthogonally to trailing surface 116 and extends in an anterior direction from the spacer 110. Further, instrument 130 extends generally parallel to upper and lower surfaces 111, 112, but in other examples, the instrument may extend in an angled direction, either superiorly, inferiorly, or laterally to spacer 110. Proximal end 134 of shaft 131 may include raised portion 136 for easier gripping. Raised portion 136 may further include an attachment mechanism to attach to a separate handle such as a quick connect handle (not shown), if further length of insertion instrument 130 is required during a procedure. However, in other examples, shaft 131 may be flat and may not include a raised portion. In some embodiments, instrument 130 may be used as a driver to drive one or more of screws 125 into their fully inserted positions after instrument 130 is separated from spacer 130.

Figure 6:
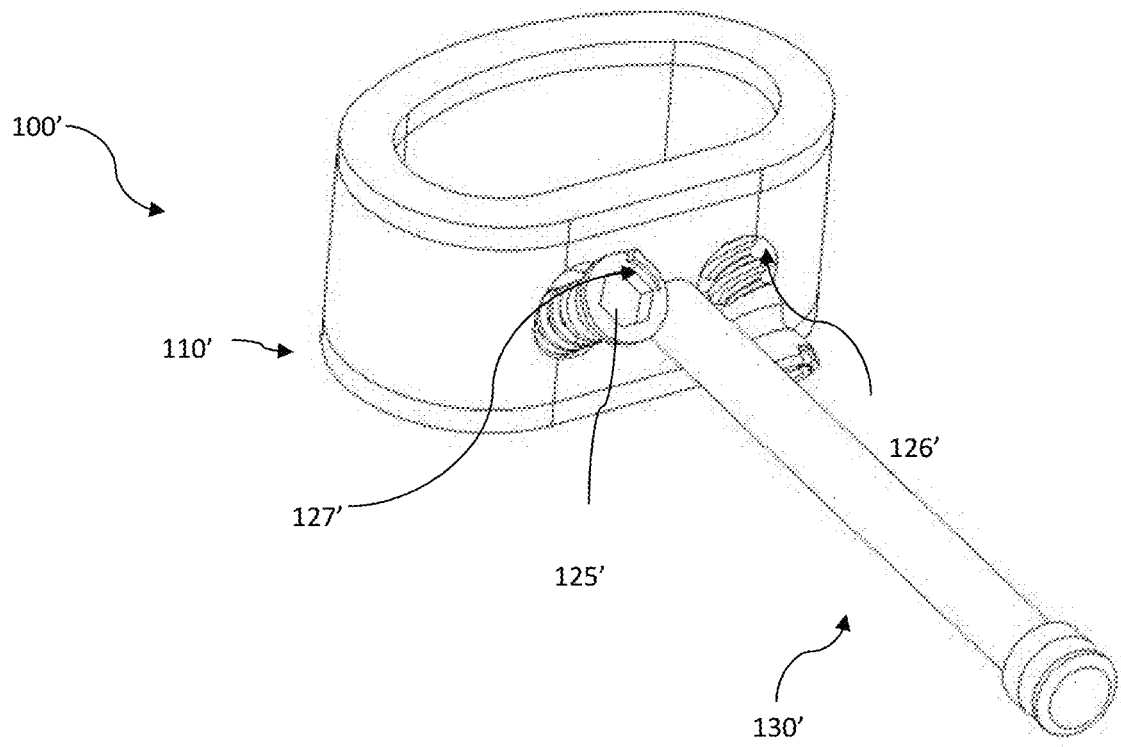
FIG. 6 is a front perspective view of an intervertebral implant system according to another embodiment of the present invention.
Figure 7:
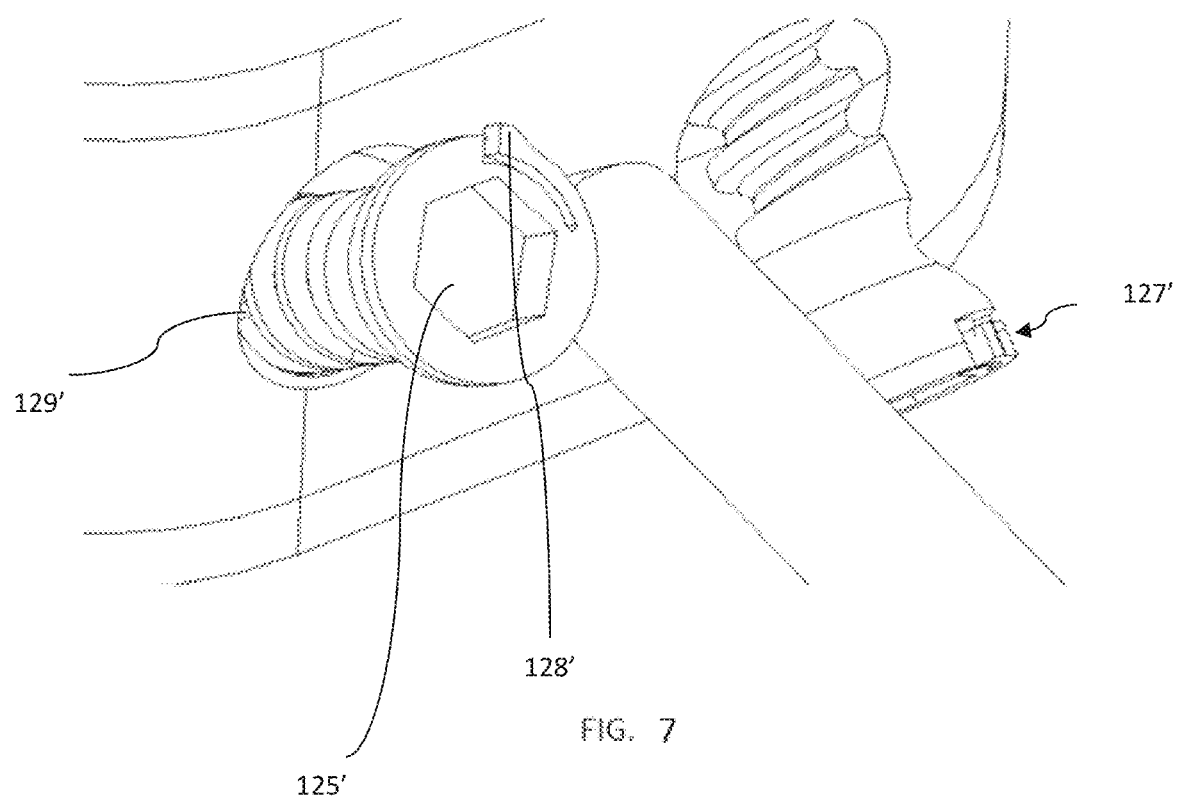
FIG. 7 is an enlarged front perspective view of a portion of the intervertebral implant system of FIG. 4.

FIGS. 6-7 depict an intervertebral implant system 100' according to another embodiment of the present invention. Implant system 100' has similar features to those described above in connection with implant system 100. Screws 125' are initially monolithically connected to spacer 110' by frangible connection 129' that is constructed to break or shear upon a force applied to one of spacer 110' and screws 125'. In the illustrated embodiment, frangible connection 129' is similar to frangible connection 129 of spacer 110 and is a radial flange of the material extending from the shaft or a thread on the shaft of screw 125' to a surface of hole 126'. In other arrangements, the frangible connection 129' can be configured with different geometries, including an annular flange, and one or more connections 129' can be employed.

Screws 125' each include a locking mechanism 127' to secure the screws within spacer 110' after implantation. As best shown in FIG. 6, locking mechanism 127' is located on the head of each screw 125' and includes flange 128' extending further radially outward from the rest of the head of screw 125'. Flange 128' has an outwardly extending protrusion which, when it contacts an inner surface of hole 126', causes flange 128' to flex inward toward screw to produce a friction fit between the head of screw 125 and hole 126'. Holes 126' may also include a groove (not shown) for flange 128' to snap into. Flange 128' is provided to inhibit backout of screw 125' once it is inserted into spacer 110'. Other types of known anti-backout mechanisms, such as split rings, spring bars, washers, rotatable cover plates, etc., can also be used. Snap fits, cover plates, and/or other compression technology known in the art may be used.

A method of implanting intervertebral implant systems 100, 100' in the lumbar spine from an anterior surgical approach will now be described with reference to system 100. At least a portion of an intervertebral disc between adjacent vertebrae is removed using tools and techniques known in the art. Intervertebral implant system 100 is provided in a sterile kit. Once removed from the packaging, instrument 130 is connected with a quick connect handle. In some instances, a tube can be inserted over instrument 130 for added stability during insertion. Spacer 110 and screws 125 are then inserted into the prepared disc space using insertion instrument 130. This can include impacting a proximal end of instrument 130. Once spacer 110 is located in the disc space, the surgeon can use instrument 130 to manipulate and stabilize spacer 110 in the desired location.

The surgeon then torques each of screws 125 with a driver, such as by manually driving the screw or using a power driver, such that attachment between the screws and spacer 110 is sheared. Screws 125 continue to be torqued and rotated into engagement with the respective vertebrae. Because the screws are already angled within spacer 110, the screws are positioned having the appropriate and correct trajectory into the bone. After the implant 100 is secured within the bone, the surgeon may then cantilever and break off instrument 130. Breaking off instrument 130 may allow for a flat surface, such that the break is clean without leaving any sharp edges. Instrument 130 is then removed from the patient. In certain embodiments, removal of instrument 130 can be done at an earlier stage so that it can be used as a driver for one or more screws 125. A separate mechanism for preventing backing out of screws 125 may then be attached to the implant, if desired.

It will be understood that the same or similar methods may be employed to install the implant system 100 at any level of the spine, and from any surgical approach, including lateral, without departing from the scope of the present invention. More specifically, it is contemplated that implant system 100 may be implanted from an anterior, posterior, posterior-lateral, lateral, or other surgical approach.

FIGS. 8-11 depict an intervertebral implant system 200 according to an embodiment of the present invention. Implant system 200 includes spacer 210, fixation members or anchor blades 245 and insertion instrument 230. Spacer 210 includes top and bottom surfaces 211, 212, respectively, leading surface 215, a trailing surface 216 opposite leading surface 215, and lateral surfaces 214 extending between the leading and trailing sides 215, 216. In the illustrated embodiment, spacer 210 has a generally rounded, oblong shape with lateral surfaces 214 being rounded. Alternatively, spacer 210 may be generally, square, rectangular, kidney, oval, circular, or other geometric shape in the superior view. Top and bottom surfaces 211, 212 may be flat, concave, convex, or any other shape in the anterior or lateral views and may include teeth or ridges for more secure placement against endplates of the adjacent vertebrae. In particular, in a lateral view, top and bottom surfaces 211, 212 may be curved or angled to give spacer 210 a lordotic shape.

Figure 8:
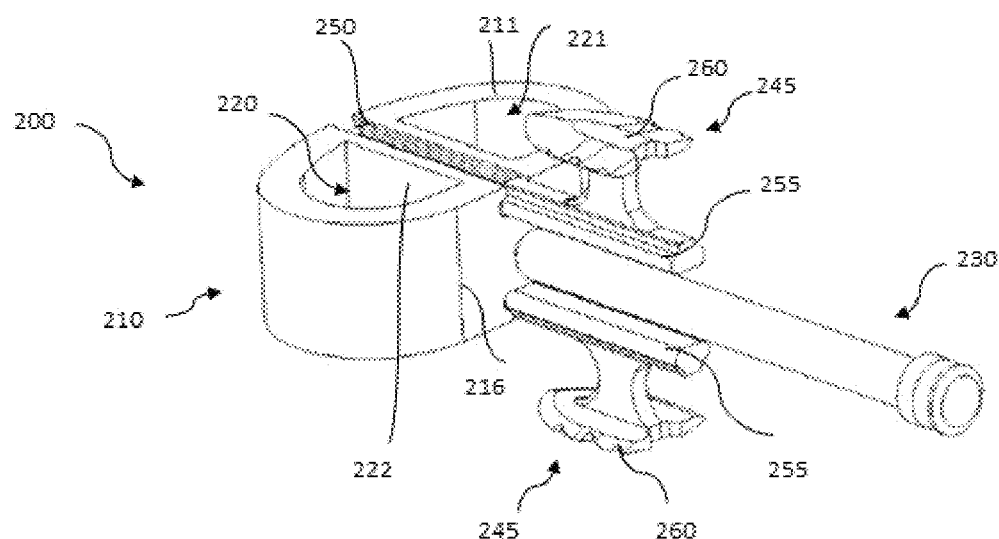
FIGS. 8-11 are front perspective, side perspective, rear elevational, and enlarged front elevational views, respectively, of an intervertebral implant system according to another embodiment of the present invention.
Figure 9:
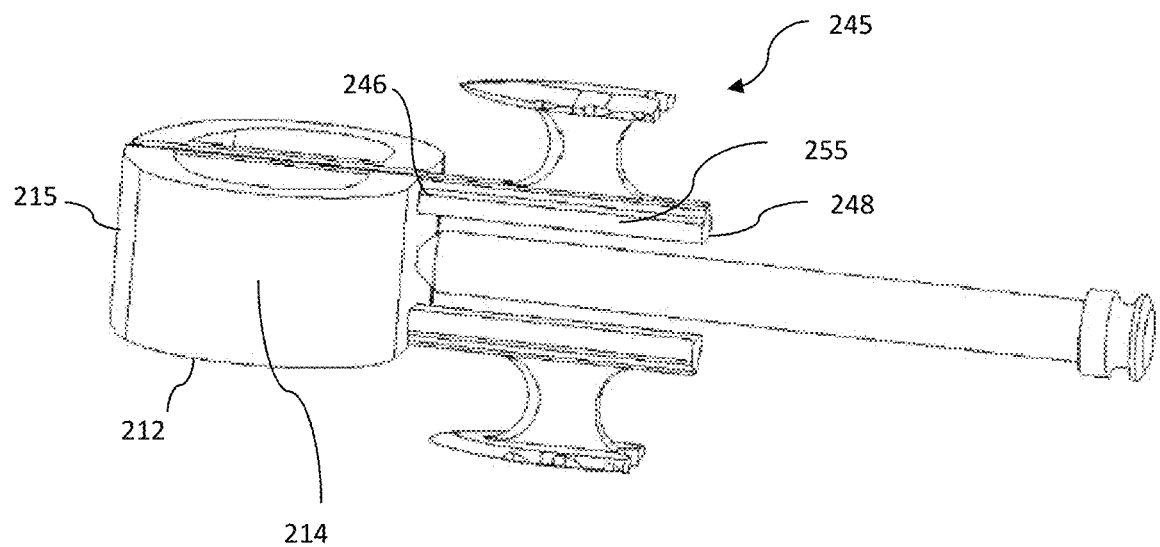
Figure 10:
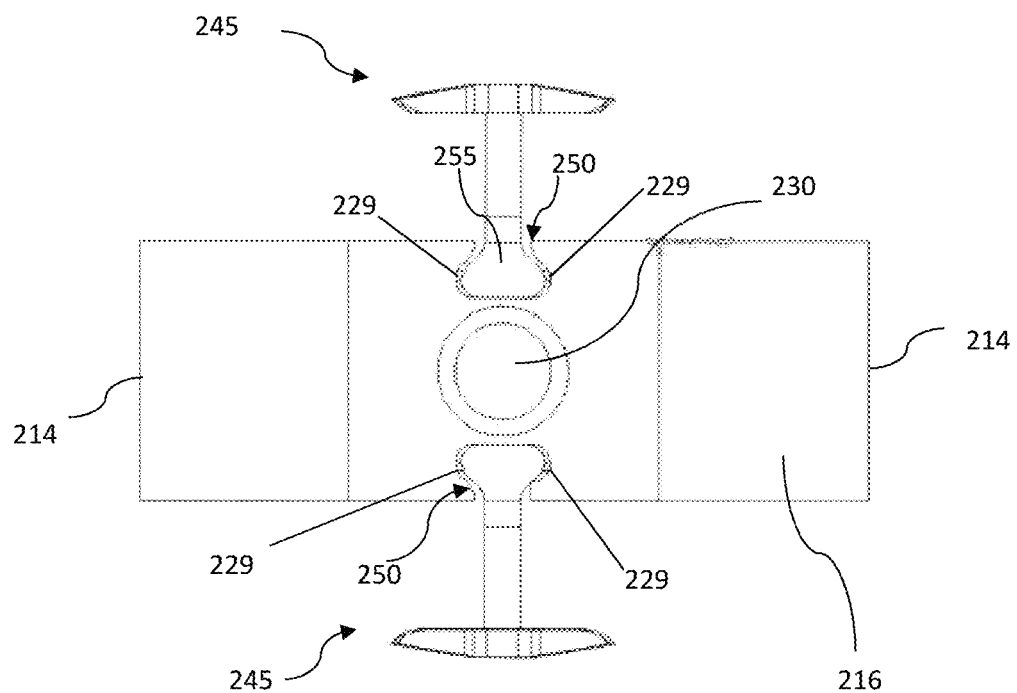
Figure 11:
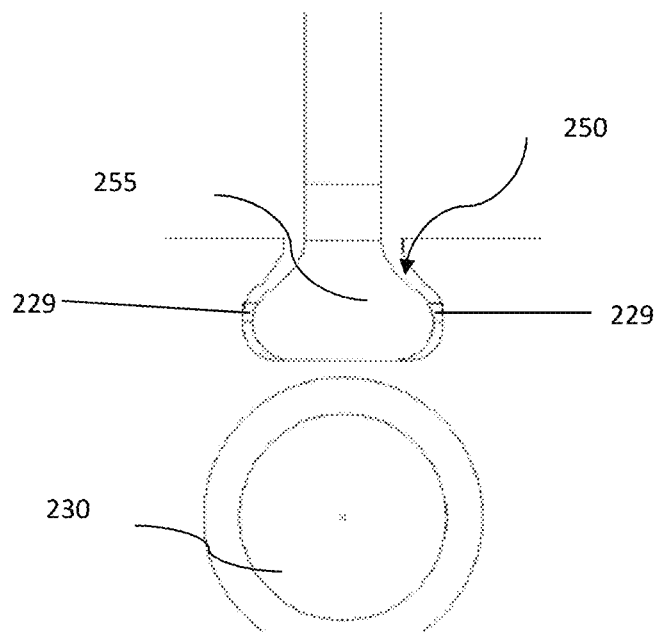

Spacer 210 further includes channels or tracks 250 that extend across spacer 210 between and intersect with both leading side 214 and trailing side 216. As shown in FIGS. 8-9, channels 250 are dovetail slots that are formed in spacer 210 in a truncated I-beam shape. However, in other examples, the channels 250 may have a variety of shapes, including circular, rectangular, keyhole, T-shaped, etc. Each channel is preferably configured to have an enlarged profile away from the adjacent surface so that an anchor disposed therein can be secured from migrating out of that channel toward the surface. Each dovetail slot is configured to slideably engage with a mating feature on an anchor 245, described in detail below. Spacer 210 includes two channels, one channel 250 that is open toward top surface 211 of the spacer and extends across top surface 211, and one channel 250 that is open toward bottom surface 212 of the spacer and extends across bottom side 212. Although in other examples, there may be more or less of channels 250.

As shown in FIG. 8, each channel 250 may extend about a central axis that is perpendicular to leading surface 214. However, in other examples, the central axis of the channels may be angled, i.e. forms a non-perpendicular angle, with respect to leading surface 214. Channels 250 may extend across top and bottom surfaces 211, 112 along an axis that extends straight through spacer 210 from trailing surface 216 to leading surface 214. Although, in other examples, the channels may be configured to extend from trailing surface 216 to leading surface 214 in a variety of angles. Further, each channel 250 may have a perimeter about its central axis that is not fully enclosed within spacer 210 at any location along its central axis so that it is open in the superior or inferior direction, as the case may be.

Spacer 210 further includes openings 220, 221 extending from top surface 211 to bottom surface 212 and positioned on lateral sides of channels 250. Openings 220, 221 are surrounded by inner surfaces 222 and are shaped as semi-ovals; however, in other examples, the openings may be shaped as generally circular, rectangular, or any other shape. Openings 220, 221 may allow for receipt of bone in-growth material. Additionally, instrument 230 is similar to instrument 130 and functions in the same manner.

Anchor blades 245 are used as a fixation method with spacer 210. Anchor 245 may include an interconnection portion 255 extending between leading end and trailing ends 246, 248. Interconnection portion 255 is shaped and sized to matingly attach with the channels 250 of spacer 210. In the present embodiment, the interconnection portion is a dovetail beam 255 that can slideably attach to the plates and spacers.

Anchor 245 can include a stop feature, such as a flange, near trailing end 248 to prevent the anchor from migrating too far posteriorly into prosthesis 210 after implantation. Anchor 245 can further include a locking feature, such as a flexible tab disposed near the trailing end 248 of the dovetail beam 255, to prevent the anchor from migrating anteriorly after implantation. The stop feature and the flexible tab can cooperate with spacer 210 to maintain anchor 255 in its implanted position in the spacer. Anchor 245 also includes a fixation portion 260 that secures anchor 245 to an adjacent vertebra. Fixation plate 260 may be sharpened around a portion of its profile to create a cutting edge to cut through bone. The anchors and other aspects of system 200 are further disclosed in U.S. Pat. No. 8,349,015, issued on Jan. 8, 2013, and titled "Intervertebral Implant With Integrated Fixation," the disclosure of which is hereby incorporated by reference herein.

As shown in FIGS. 8-11, anchors 245 are each positioned with a portion of interconnection portion 255 inserted in and frangibly attached to channel 250. This can be done during a 3D printing procedure by including at least one frangible connection 229 between anchor 245 and spacer 210. In the illustrated embodiment, frangible connection 229 is a flange of the material extending from interconnection portion 255 to channel 250 that bridges the anchor and the spacer. This flange can be perpendicular to the interconnection portion axis or angled thereto. Multiple connections 229 can be utilized and spaced apart about the interconnection portion 255. However, a single connection 229 can also be employed. Once the frangible connection is broken between spacer 210 and interconnection portion 255, the interconnection portion can slide within channel 250 without interference. The surface area of the connection can be small enough so that the connection shears upon a force applied to the proximal end of anchor 245, but large enough to withstand typical forces that may be applied, purposefully or incidentally, to anchor 245 during initial insertion of spacer 210. In other arrangements, the frangible connection can be between the bottom surface of leading end 246 of interconnection portion 255 and the adjacent bottom surface of channel 250.

After inserting the implant system into the prepared disc space, anchors 245 can be driven into the bone, such as by manually driving anchors 245 or using a pneumatic driver, such that the blade slides into position further distally within channel 250 and the monolithic attachment of the anchors with spacer 210 is broken. As a result, a proximal portion near trailing end 248 of anchor 245 is closer to trailing side 216 and within channel 250.

Although described above with reference to illustrated anchor 245, other embodiments of anchor blades work in conjunction with implant system 200. Any sort of staple, blade, or anchor that is eventually inserted into connection with spacer 210 and one or more adjacent vertebrae can be 3D printed and frangibly connected in the manner discussed above. Additionally, a spacer may be configured such that it includes both screw fixation members and blade fixation members. In this manner, a spacer similar to spacer 210 may include screws similar to screws 125 or screws 125'. The screws may be located on either side of instrument 230 on trailing surface 216. Further, the screws may be angled, such that one screw extends superiorly and the other screw extends inferiorly. Both the blades and screws may be formed monolithically with the spacer or one fixation mechanism, such as one of the screws and blades, may be monolithic, while the spacer is designed to allow for insertion of the non-monolithic, standalone fixation component.

Implant systems 100, 100', and 200, as well as others according to the present inventions, may include one or more radiographic markers on the top surfaces of spacers 110, 110', and 210 (not shown). Additionally, the spacers may include serrations on various surfaces, i.e. top and bottom surfaces, to allow for fixation with adjacent vertebrae.

Although shown as anterior implants, intervertebral systems 100, 100', 210 may be configured and dimensioned for lateral spinal surgery. In this manner, the system, in particular spacers 110, 110', 210 may have dimensions that are greater in the medial-lateral direction and lesser in the anterior-posterior direction as compared to spacer 110, 110', 210.

In other embodiments, spacers 110, 110', 210 may include an attachment mechanism to allow for attachment of a retaining mechanism or plate at trailing surface 116. The retaining mechanism may include clips, positioned for example on a top surface, bottom surface, and/or lateral surfaces to attach to fit into recesses in corresponding locations on spacer 100. Such retaining mechanisms are disclosed in U.S. Pat. No. 9,480,577, issued on Nov. 1, 2016, and titled "Retaining Mechanism, Implant, and Tool," and U.S. Application No. 62/478,162, filed on Mar. 29, 2017, and titled "Spinal Implant System," the disclosures of both of which are hereby incorporated by reference herein.

A method of implanting intervertebral implant system 200 in the lumbar spine from an anterior surgical approach includes first removing at least a portion of an intervertebral disc between adjacent vertebrae. Intervertebral implant system 200, provided in a sterile kit and including spacer 210, anchor blades 245, and instrument 230, is then inserted into the prepared disc space using insertion instrument 230 for manipulation. Once spacer 210 is in the disc space, the surgeon can use instrument 230 to stabilize the spacer 210 in the desired location. The surgeon then drives anchor blades 245 in a posterior direction to engage the adjacent vertebrae using guiding instruments, which can be equipped to handle impaction during the insertion. In doing so, the attachment between anchors 245 and spacer 210 is sheared and anchors 245 are moved into full connection with spacer 210 and the respective vertebrae. After implant 200 is secured within the bone, the surgeon may then break off instrument 230. Breaking off instrument 230 may allow for a flat surface, such that the break is clean. Instrument 230 is then removed from the patient. A mechanism for preventing backing out of anchors 245, such as a cover plate, may optionally be attached to implant.

Figure 12:
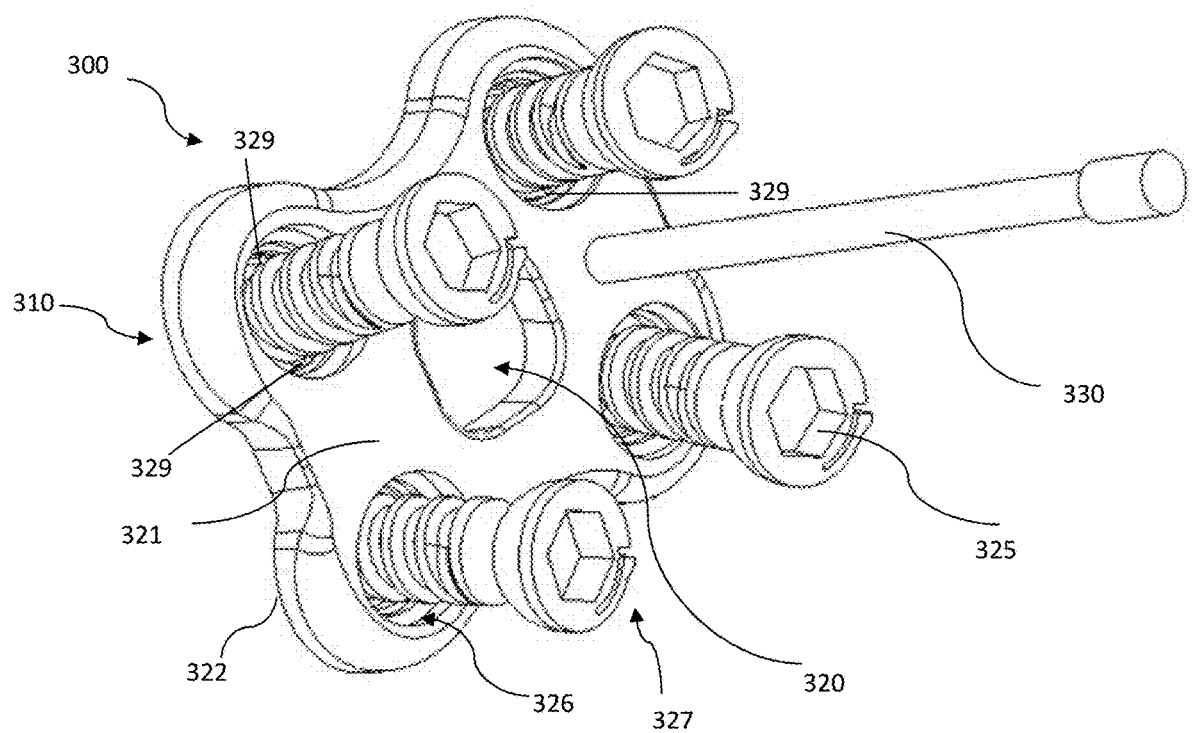
FIG. 12 is a top perspective view of a bone plate system according to another embodiment of the present invention.

FIG. 12 shows a spinal fusion plate system 300 according to an embodiment of the invention that may be used to stabilize or fuse vertebral bodies of the spine. The system is configured to span across and fixate at least two vertebrae of the spine. The system comprises a plate 315 having screws 325 extending into the plate and instrumentation 330. Plate 315 includes an upper surface or anterior surface 321 facing the patient's soft tissue when installed and a lower surface or posterior surface 322 facing the vertebral bodies to be immobilized. The upper surface 321 and lower surface 322 are interconnected by curved side walls and end walls to form a generally rectangular shape that is symmetrical about a midline. The gently curved structure of plate 315 complements the natural curved structure of the vertebral bodies and lordotic curvature of the spine. The corners of the plate are rounded to reduce irritation of the surrounding tissue. Plate 315 has a low profile to minimally impinge on adjacent tissue.

Plate system 300 further includes screws 325 similar to screws 125 and including a locking feature 327 similar to locking feature 127'. Screws 325 are initially monolithically connected to spacer 310 by frangible connection 329, similar to frangible connection 129 of spacer 110. Connection 329 is constructed such that it can break or shear upon a force applied to one of spacer 310 and screws 325. In the illustrated embodiment, there are multiple connections 329 each extending from screw 325 to an inner surface of hole 326. In other arrangements, more or less frangible connections having the same or different configurations can be employed, as described above.

In the illustrated embodiment, four screws 325 are positioned within holes 326, the screws and holes extending from upper surface 321 to lower surface 322. Screws 325 may be fixed and/or variable angle screws. Screws 325 are spaced apart and each one is positioned near a curved corner of plate 315. Opening 320 is positioned generally centrally on plate 315 and extends from upper surface 321 to lower surface 322. Opening 320 reduces the overall weight of plate 315 and provides a visualization pathway to monitor bone graft progress between the vertebral bodies. Screws 325 are frangibly connected with plate 310 in a manner similar to screws 125 with spacer 120.

Plate system 300 further includes instrument 330 similar to instrument 130 of implant system 100. The frangible connection between plate 310 and instrument 330 is similar to that of spacer 110 and instrument 130. Instrument 330 is positioned on upper surface 321 and extends anteriorly away from the upper surface. Instrument 330 may be positioned in between two screws 325 or in any location on plate 300 where it can be used for manipulation of plate 300 by a user without interfering with the manipulation of screws 325.

A method of implanting bone plate system 300 includes placing plate 310 adjacent to a vertebral column using instrument 330 as a guide and/or handle for insertion. The placement of the plate 310 relative to the vertebral bone in a patient may be determined based on a pre-operative examination of the patient's spine using non-invasive imaging techniques known in the art. Any additional preparation may be done around the desired vertebrae prior to positioning plate 310. Once plate 310 is appropriately positioned, screws 325 are torqued, such that the attachment of screws 325 with plate 310 is sheared. Screws 325 are further torqued to engage the bone. After plate 310 is secured, instrument 330 is broken off from the implant.

Figure 13:
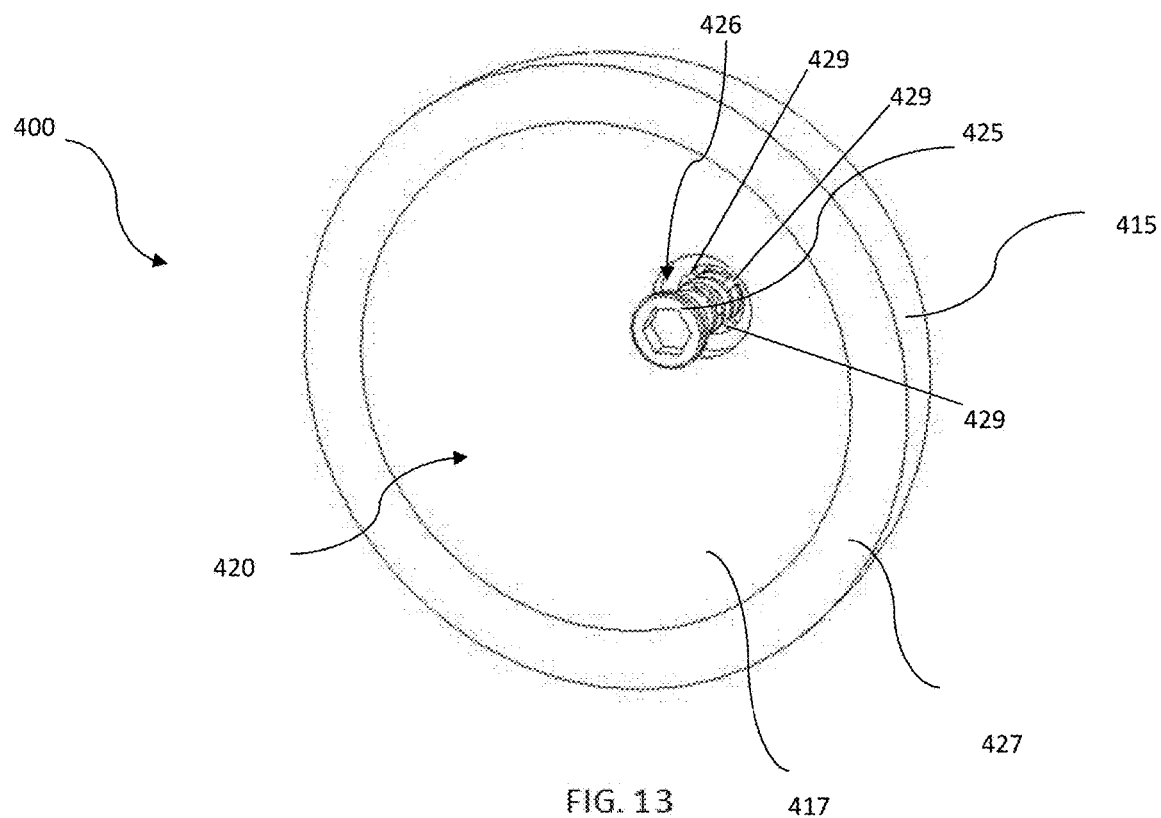
FIGS. 13-15 are front perspective, side perspective, and sectional side views, respectively, of an acetabular implant system according to an embodiment of the present invention.
Figure 14:
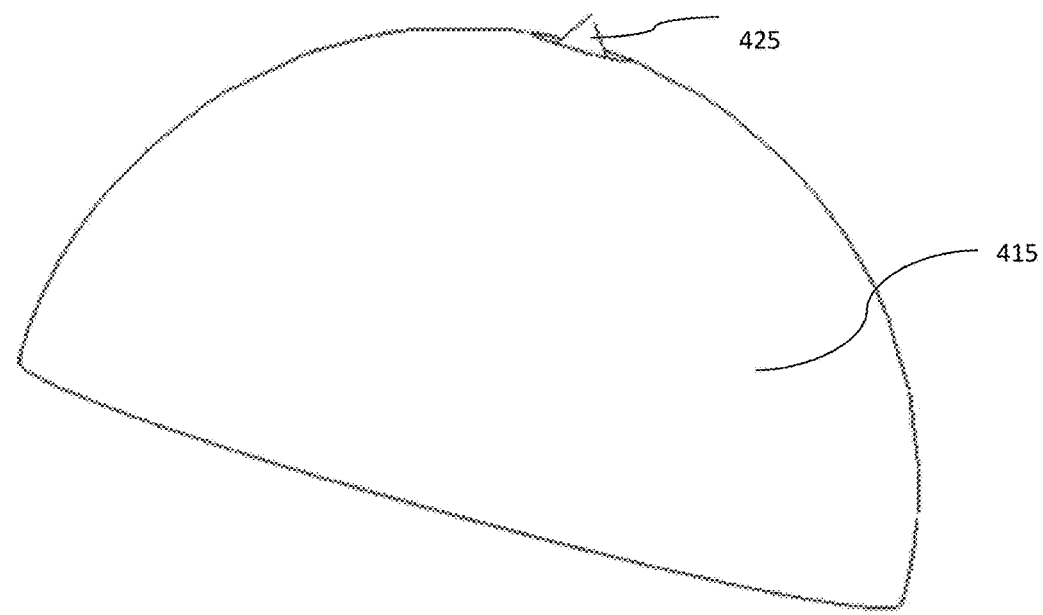
Figure 15:
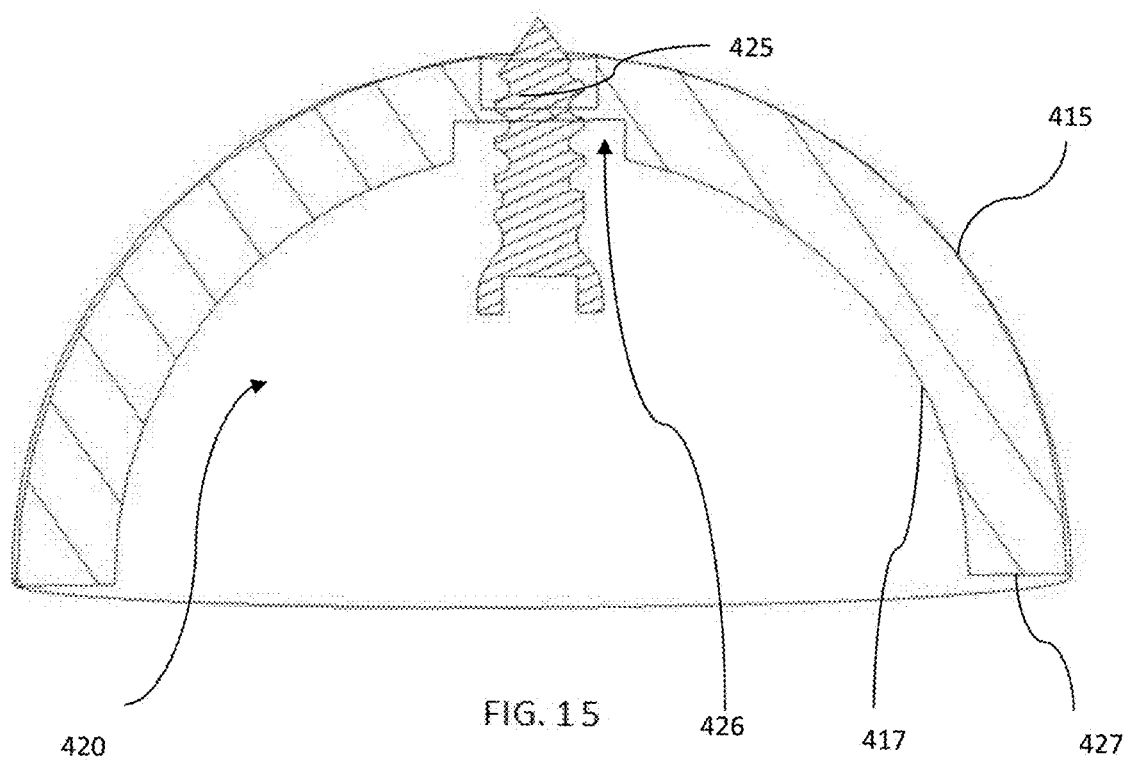

FIGS. 13-15 depict a prosthetic acetabular cup implant system 400 according to an embodiment of the present invention. Implant system 400 includes an acetabular cup 410 and screw 425 positioned in hole 426. Screw 425 is frangibly connected with cup 410 by frangible connections 429 in a manner similar to screws 125 with spacer 110. In the illustrated embodiment, each frangible connection 429 is radial flange of the material extending from the shaft or a thread on the shaft of screw 425 to a surface of hole 426. The flange can be perpendicular to the screw axis or angled thereto. Although shown as having more than one connection 429, the system 400 may include a single connection, such as a single annular connection.

Acetabular cup 410 is a part-spherical cup adapted for location in an acetabulum and having a rounded outer surface 415 and an inner bearing surface 417 to receive a bearing liner and a part-spherical ball head which can be attached to a prosthetic stem for location in a femur. Acetabular cup further defines an opening 420 due to the semi-spherical shape of the cup. Acetabular cup 410 further includes flat surface or rim 427 extending between outer surface 415 and inner surface 417.

Hole 426 and screw 425 extend along a central axis from inner surface 417 to outer surface 415. In the illustrated embodiment, there is one screw 425 located generally centrally at a midpoint of acetabular cup 410. Screw 425 is formed monolithically with acetabular cup 410. Screw 425 is initially positioned such that a portion of the screw shaft is enclosed within acetabular cup 410 and the tip extends proximally from the acetabular cup. Further, the head of the screw is positioned within opening 420.

In the illustrated embodiment, screw 425 is similar to screw 125, but implant system 400 can also include a screw similar to screws 125', in which a locking mechanism is including within the screw and/or hole to secure the screw within acetabular cup 410. Additionally, although the illustrated embodiment there is only one screw 425, the system may include multiple screws 425 and holes 426 spaced apart on acetabular cup 410. It is also contemplated that an instrument like instrument 130 be connected with a portion of cup 410, such as rim 427 so as not to interfere with bearing surface 417. However, this highlights that systems in accordance with the present invention can be provided with just an implant and fixation member(s), and without an insertion instrument. Likewise, an insertion instrument can be provided in a system with an implant but without fixation members if none are applicable or desired.

A method of implanting hip implant system 400 includes preparing an acetabulum for insertion of implant system 400. Cup 410 is then inserted into the patient, and screw 425 is torqued. The torque shears the attachment of screw 425 with cup 410. Screw 425 is torqued further such that it engages the bone to provide securement of the implant to the bone.

Implant systems in accordance with the present inventions are formed using three-dimensional (3D) printing to produce a monolithic structure comprised of a spacer, one or more fixation members, and/or an insertion instrument, the fixation members and instrument being frangibly coupled to the spacer. The implant system does not experience any additional fixation process to provide for the monolithic construction and as such the monolithic connection is not the result of welding, fusing, cement, or any similar process beyond the particulars of the ALM process used during construction. The systems can be comprised of a porous metal or can have a solid internal core with a porous metal surface such as a porous titanium alloy, including Tritanium® by Howmedica Osteonics Corporation. The implant systems may be comprised of metal, such as titanium, ceramic, glass, polymer, or any other material known for use in the human body and capable of utilization in a 3D printing technique. The implant systems may also comprise one or more surface treatments to encourage bony attachment, such as porous coating, plasma spray coating, hydroxyapatite, or tricalcium phosphate.

In preferred arrangements, any of the present implants systems can be formed, at least in part, in a layer-by layer fashion using an additive layer manufacturing (ALM), i.e. 3D printing, process using a high energy beam, such as a laser beam or an electron beam. Such ALM processes may be but are not limited to being powder-bed based processes including but not limited to selective laser sintering (SLS), selective laser melting (SLM), and electron beam melting (EBM), as disclosed in U.S. Pat. Nos. 7,537,664 and 9,456,901, the disclosures of each of which are hereby incorporated by reference herein, or other ALM processes such as but not limited to powder-fed based processes including but not limited to fused filament fabrication (FFF), e.g., fused deposition modeling (FDM).

The implants and systems may be constructed of porous geometries which have been digitally modeled using unit cells, as further described in U.S. Pat. Nos. 9,180,010 and 9,135,374, the disclosures of each of which are hereby incorporated by reference herein. A first layer or portion of a layer of powder is deposited and then scanned with a high energy beam to create a portion of a plurality of predetermined unit cells. Successive layers of powder are then deposited onto previous layers of the powder and also may be individually scanned. The scanning and depositing of successive layers of the powder continues the building process of the predetermined porous geometries. As disclosed herein, by continuing the building process refers not only to a continuation of a porous geometry from a previous layer but also a beginning of a new porous geometry as well as the completion of a porous geometry. The porous geometries of the formed porous layers may define pores that may be interconnecting to provide an interconnected porosity. Of course, implants can also be made to be solid with or without porous portions.

In accordance with the present teachings, frangible fixation members and/or insertion instruments may be used for other prosthetic implants throughout the body. The present invention is not limited to any particular type of implant and is not limited to surgical applications. For example, it is contemplated that the present invention can be implemented in different spinal implants, such as the implants disclosed in U.S. application Ser. No. 14/994,749, filed on Jan. 13, 2016, and titled "Spinal Implant with Porous and Solid Surfaces," the disclosure of which is hereby incorporated by reference herein. Moreover, other areas and uses may include unicompartmental knee replacement implants, bicompartmental knee replacement implants, tricompartmental knee replacement implants, total knee replacement implants, patellofemoral replacement implants, shoulder implants, hip implants, cortical and spinal plates, base plates, etc. An implant in accordance with the present application can be a patient-specific implant generated from CAD files, for example, so that it is unique for a particular patient and application. Other nonsurgical applications are also contemplated. For example, an L bracket may be monolithically formed with a screw using additive layering manufacturing, as described above. This arrangement can be used to insert a screw into a wall. The screw may be frangibly connected to the L bracket such that torqueing the screw breaks the connection with the L bracket.

Systems in accordance with the present invention allow pre-packaging of the entire monolithic implant system, which can reduce manufacturing cost as well as inventory of implants and instruments as part of an instrumented fusion surgery. A system can be offered pre-packaged as a set in a sterile package. This allows the packaged implant system, provided in a blister package for example, to be supplied to an operating room and opened immediately prior to use in a surgical procedure.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the claims below.

The invention claimed is:

1. A method comprising:
   providing a surgical implant system including an implant, a bone screw for securing the implant to tissue, and an insertion instrument, wherein the implant is monolithically connected to the bone screw at a first frangible connection and the implant is monolithically connected to the insertion instrument at a second frangible connection, such that the implant, the bone screw, and the insertion instrument together comprise a single monolithic structure; and packaging the surgical implant system in a single package.

2. The method of claim 1, wherein the packaging step results in a sterile kit.

3. The method of claim 1, further comprising the step of 3D printing the surgical implant system.

4. The method of claim 1, wherein at least a portion of the implant is porous.

5. The method of claim 4, wherein at least a portion of the implant has an interconnected porosity.

6. The method of claim 1, wherein at least a portion of the implant is solid.

7. The method of claim 1, wherein the surgical implant system includes both solid and porous portions.

8. The method of claim 7, wherein the bone screw is solid.

9. The method of claim 7, wherein the insertion instrument is solid.

10. The method of claim 7, wherein at least a portion of the implant is porous.

11. The method of claim 1, wherein the packaging step includes forming a blister package.

12. A method comprising:

providing a surgical implant system including an implant and a bone screw for securing the implant to tissue, wherein the implant is monolithically connected to the bone screw at a frangible connection such that the implant and the bone screw together comprise a single monolithic structure; and packaging the surgical implant system in a single package.

13. The method of claim 12, further comprising the step of 3D printing the surgical implant system.

14. The method of claim 12, wherein a first portion of the surgical implant system is solid and a second portion of the surgical implant system is porous.

15. The method of claim 12, wherein the packaging step includes forming a blister package.

16. The method of claim 12, wherein the packaging step results in a sterile kit.

17. A method comprising:

providing a surgical implant system including an implant and an insertion instrument, wherein the implant includes a body that is monolithically and directly connected to the insertion instrument at a frangible connection such that the implant and the insertion instrument together comprise a single monolithic structure; and packaging the surgical implant system in a single package.

18. The method of claim 17, wherein the packaging step results in a sterile kit.

19. The method of claim 17, further comprising the step of 3D printing the surgical implant system.

20. The method of claim 17, wherein the packaging step includes forming a blister package.

* * * * *